(12) United States Patent
Beulke et al.

(10) Patent No.: US 6,902,572 B2
(45) Date of Patent: Jun. 7, 2005

(54) ANCHORING MECHANISMS FOR INTRAVASCULAR DEVICES

(75) Inventors: Mel R. Beulke, Bloomington, MN (US); Brian J. Lowe, Zimmerman, MN (US); Steven M. Spencer, Minneapolis, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 155 days.

(21) Appl. No.: 10/405,546

(22) Filed: Apr. 2, 2003

(65) Prior Publication Data

US 2004/0199198 A1 Oct. 7, 2004

(51) Int. Cl.$^7$ .............................................. A61M 29/00
(52) U.S. Cl. ...................................... 606/200; 606/159
(58) Field of Search .................................. 606/200, 159

(56) References Cited

U.S. PATENT DOCUMENTS

| | | |
|---|---|---|
| 3,472,230 A | 10/1969 | Fogarty |
| 3,952,747 A | 4/1976 | Kimmell, Jr. |
| 3,996,938 A | 12/1976 | Clark, III |
| 4,046,150 A | 9/1977 | Schwartz et al. |
| 4,425,908 A | 1/1984 | Simon |
| 4,590,938 A | 5/1986 | Segura et al. |
| 4,619,246 A | 10/1986 | Molgaard-Nielsen et al. |
| 4,650,466 A | 3/1987 | Luther |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,807,626 A | 2/1989 | McGirr |
| 4,842,579 A | 6/1989 | Shiber |
| 4,873,978 A | 10/1989 | Ginsburg |
| 4,921,478 A | 5/1990 | Solano et al. |
| 4,921,484 A | 5/1990 | Hillstead |
| 4,926,858 A | 5/1990 | Giffort, III et al. |
| 4,969,891 A | 11/1990 | Gewertz |
| 4,998,539 A | 3/1991 | Delsanti |
| 5,002,560 A | 3/1991 | Machold et al. |
| 5,011,488 A | 4/1991 | Ginsburg |
| 5,053,008 A | 10/1991 | Bajaj |
| 5,059,205 A | 10/1991 | El-Nounou et al. |
| 5,071,407 A | 12/1991 | Termin et al. |
| 5,100,423 A | 3/1992 | Fearnot |
| 5,102,415 A | 4/1992 | Guenther et al. |
| 5,133,733 A | 7/1992 | Rasmussen et al. |
| 5,147,379 A | 9/1992 | Sabbaghian et al. |

(Continued)

FOREIGN PATENT DOCUMENTS

| | | |
|---|---|---|
| DE | 28 21 048 | 7/1980 |
| DE | 34 17 738 | 11/1985 |
| DE | 40 30 998 A1 | 10/1990 |

(Continued)

OTHER PUBLICATIONS http://www.google.com/search?hl=en&q=define%3ALeaf+spring, Dec. 6, 2004.*

(Continued)

Primary Examiner—Paul B. Prebilic
(74) Attorney, Agent, or Firm—Crompton Seager & Tufte LLC (57) ABSTRACT

Anchoring mechanisms for limiting travel of an intravascular device along an elongated member such as a guidewire or guide catheter are disclosed. The anchoring mechanism may include a leaf spring that can be actuated between an unlocked position and a locked position. In the unlocked position, the leaf spring is slidably and rotationally disposed along the elongated member. In the locked position, the leaf spring is releasably secured to the elongated member, preventing movement thereon. The leaf spring can be attached directly to the intravascular device, or can be formed as a separate member and used as a stopper mechanism to limit travel of the intravascular device along the elongated member.

2 Claims, 6 Drawing Sheets

U.S. PATENT DOCUMENTS

| | | |
|---|---|---|
| 5,152,771 A | 10/1992 | Sabbaghian et al. |
| 5,152,777 A | 10/1992 | Goldberg et al. |
| 5,160,342 A | 11/1992 | Reger et al. |
| 5,224,953 A | 7/1993 | Morgentaler |
| 5,324,304 A | 6/1994 | Rasmussen |
| 5,329,942 A | 7/1994 | Gunther et al. |
| 5,330,484 A | 7/1994 | Gunther |
| 5,354,310 A | 10/1994 | Garnie et al. |
| 5,375,612 A | 12/1994 | Cottenceau et al. |
| 5,376,100 A | 12/1994 | Lefebvre |
| 5,415,630 A | 5/1995 | Gory et al. |
| 5,421,832 A | 6/1995 | Lefebvre |
| 5,423,742 A | 6/1995 | Theron |
| 5,449,372 A | 9/1995 | Schmaltz et al. |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,634,942 A | 6/1997 | Chevillon et al. |
| 5,658,296 A | 8/1997 | Bates et al. |
| 5,662,671 A | 9/1997 | Barbut et al. |
| 5,669,933 A | 9/1997 | Simon et al. |
| 5,681,347 A | 10/1997 | Cathcart et al. |
| 5,695,519 A | 12/1997 | Summers et al. |
| 5,709,704 A | 1/1998 | Nott et al. |
| 5,720,764 A | 2/1998 | Naderlinger |
| 5,728,066 A | 3/1998 | Daneshvar |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,795,322 A | 8/1998 | Bouewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran |
| 5,836,968 A | 11/1998 | Simon et al. |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,168,604 B1 | 1/2001 | Cano |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,217,600 B1 | 4/2001 | DiMatteo |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,342,063 B1 | 1/2002 | DeVries et al. |
| 6,344,049 B1 | 2/2002 | Levinson et al. |
| 6,371,971 B1 | 4/2002 | Tsugita et al. |
| 6,425,909 B1 | 7/2002 | Dieck et al. |
| 6,494,895 B2 | 12/2002 | Addis |
| 6,506,205 B2 | 1/2003 | Goldberg et al. |
| 2002/0095174 A1 | 7/2002 | Tsugita et al. |
| 2002/0111648 A1 | 8/2002 | Kusleika et al. |

FOREIGN PATENT DOCUMENTS

| | | |
|---|---|---|
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 1 127 556 A2 | 8/2001 |
| FR | 2 580 504 | 10/1986 |
| FR | 2 643 250 A1 | 8/1990 |
| FR | 2 666 980 | 3/1992 |

| | | |
|---|---|---|
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |

OTHER PUBLICATIONS

"Atherosclerotic Disease of the Aortic Arch as a Risk Factor of Recurrent Ischemic Stroke," The New England Journal of Medicine, pp. 1216–1221 (May 1996).

"Endovascular Grafts, Stents Drive Interventional Radiology Growth," *Cardiovascular* Device Update, 2(3):1–12 (Mar. 1996).

"Protruding Atheromas in the Thoracic Aortic and Systemic Embolization," pp. 423–427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR, 141*:601–604 (Sep. 1983).

Cragg, Andrew et al., "Nonsurgical Placement of Arterial Endoprosthesis: A New Technique Using Nitinol Wire," AJR, pp. 261–263 (Apr. 1983).

Diethrich et al., "Percutaneous Techniques for Endoluminal Carotid Interventions," J. Endovasc. Surg., 3:182–202 (1996).

Fadali, A. Moneim, "A filtering device for the prevention of particulate embolization during the course of cardiac surgery," Surgery, 64(3):634–639 (Sep. 1968).

Haissaguerre et al., "Spontaneous Initiation of Atrial Fibrillation by Ectopic Beats Originating in the Pulmonary Veins," *The New England Journal of Medicine, 339* (10):659–666 (Sep. 1988).

Jordan, Jr. et al., "Microemboli Detected by Transcranial Doppler Monitoring . . . ," Cardiovascular Surgery, 7(1)33–38 (Jan. 1999).

Lesh, "Can Catheter Ablation Cure Atrial Fibrillation?" *ACC Current Journal Review*, pp. 38–40 (Sep./Oct. 1997).

Lund et al., "Long–Term Patentcy of Ductus Arteriosus After Balloon Dilation: an Experimental Study," Laboratory Investigation, 69(4):772–774 (Apr. 1984).

Marache et al., "Percutaneous Transluminal Venous Angioplasty . . . ," *American Heart* Journal , 125(2 Pt 1):362–366 (Feb. 1993).

Mazur et al., "Directional Atherectomy with the Omnicath™: A Unique New Catheter System," Catheterization and Cardiovascular Diagnosis, 31:17–84 (1994).

Moussa, MD, Issaam "Stents Don't Require Systemic Anticoagulation . . . But the Technique (and Results) Must be Optimal," Journal of Invasive Cardiol., 8(E):3E–7E, (1996).

Onal et al., "Primary Stenting for Complex Atherosclerotic Plaques in Aortic and Iliac Stenoses," Cardiovascular & Interventional Radiology, 21(5):386–392 (1998).

Theron et al., "New Triple Coaxial Catheter System for Carotid Angioplasty with Cerebral Protection," American Journal of Neuroradiology, 11:869–874 (1990).

Waksman et al., "Distal Embolization is Common After Directional Atherectomy . . . ," American Heart Journal, 129(3):430–435 (1995).

Wholey, Mark H. et al., PTA and Stents in the Treatment of Extracranial Circulation, *The* Journal of Invasive Cardiology, 8(E):25E–30E (1996).

* cited by examiner

Fig. 10

ANCHORING MECHANISMS FOR INTRAVASCULAR DEVICES

FIELD OF THE INVENTION

The present invention pertains to anchoring mechanisms for intravascular devices. More specifically, the present invention relates to anchoring mechanisms for limiting travel of an intravascular device along an elongated member disposed within a body vessel.

BACKGROUND OF THE INVENTION

Medical procedures to treat occlusive vascular diseases, such as angioplasty, atherectomy and stent deployment, routinely involve the insertion and subsequent removal of various intravascular devices. In an angioplasty procedure, for example, a physician will typically advance a guidewire having an attached embolic protection filter to a desired location within the body, and subsequently deploy a balloon catheter to dislodge embolic debris or thrombus from a lesion. In some instances, the physician may wish to deploy more than one device during the procedure. For example, if the first embolic protection filter becomes occluded with debris dislodged during the angioplasty procedure, the physician may wish to replace the occluded filter with a second filter while maintaining guidewire position.

SUMMARY OF THE INVENTION

The present invention relates to anchoring mechanisms for releasably securing an intravascular device to a guidewire disposed within the vasculature of a patient. In an exemplary embodiment of the present invention, an anchoring mechanism may comprise a leaf spring actuatable between an unlocked position and a locked position. The leaf spring may comprise a normally flat, flexible body having at least one opening configured to receive and grip the elongated member at one or more contact regions defined by the opening. In certain embodiments, the flexible body may comprise a first flat region, a second flat region, and a bend region therebetween configured to permit bending of the first flat region relative to the second flat region. In other embodiments, the flexible body may comprise a multiple leaf spring having several alternating bend regions connecting several flat regions together in alternating fashion.

The leaf spring may include one or more indentations to impart a particular degree of flexibility to the leaf spring. In certain embodiments, for example, the leaf spring may include an indentation region at or near each bend region to permit greater flexion of the leaf spring at the bend region and reduce the spring's profile. A proximal and/or distal flat region of the leaf spring configured to align perpendicularly to the elongated member may be employed to ensure proper alignment of the leaf spring along the elongated member.

In use, the leaf spring can be attached directly to an intravascular device, allowing the intravascular device to be releasably secured to the elongated member. Alternatively, the leaf spring can be formed as a separate member and used as a stopper mechanism to limit travel of the intravascular device along the elongated member. A locking tube slidably disposed about the elongated member may be utilized to actuate the leaf spring between the locked and unlocked positions within the body. In certain exemplary embodiments, the locking tube may include a bendable locking tab configured to permit the operator to withdraw the locking tube and engage the leaf spring.

DETAILED DESCRIPTION OF THE INVENTION

The following description should be read with reference to the drawings wherein like reference numerals indicate like elements throughout the several views. The detailed description and drawings illustrate exemplary embodiments of the claimed invention. The drawings, which are not necessarily to scale, depict several embodiments and are not intended to limit the scope of the invention. Although examples of construction, dimensions, materials and manufacturing processes are illustrated for the various elements, those skilled in the art will recognize that many of the examples provided have suitable alternatives that may be utilized.

Figure 1:
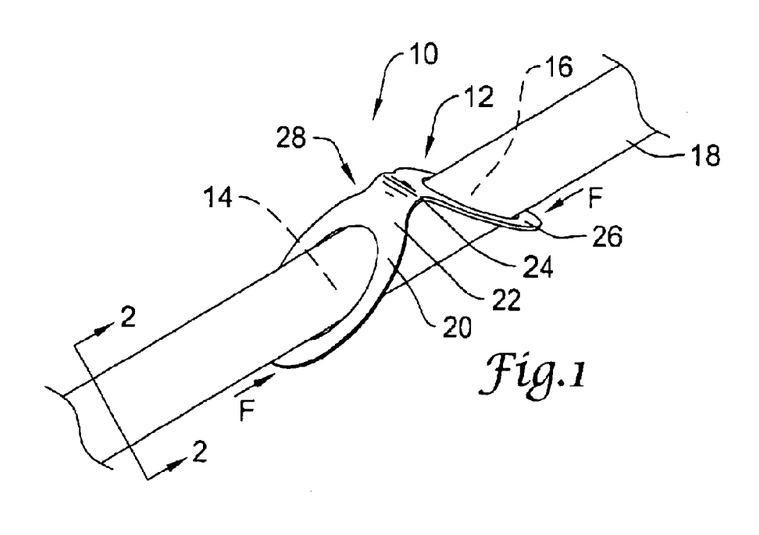
FIG. 1 is a perspective view of an anchoring mechanism in accordance with an exemplary embodiment of the present invention, wherein the anchoring mechanism comprises a single leaf spring.

FIG. 1 is a perspective view of an anchoring mechanism 10 in accordance with an exemplary embodiment of the present invention. Anchoring mechanism 10 comprises a leaf spring 12 having a number of openings 14,16 configured to slidably and rotationally receive an elongated member 18 such as a guidewire or guide catheter therethrough. Leaf spring 12 comprises a preset curved, flexible body 20 that can be deformed when the elongated member 18 is inserted through the openings 14,16 in an over-under configuration, and when a compressive force is applied to the ends of the leaf spring 12, as indicated by arrow F in FIG. 1.

Leaf spring 12 can be actuated between an unlocked position and a locked position to prevent travel of an intravascular device (not shown) along the elongated member 18. Leaf spring 12 may be utilized as either a proximal or distal stop to prevent or limit movement of an intravascular device along the elongated member 18, or can be attached to or formed integrally with an intravascular device and used as a means to directly secure the intravascular device to the elongated member 18, as shown, for example, in FIG. 3. In the exemplary embodiment illustrated in FIG. 1, leaf spring 12 is shown as a separate member configured to act as a proximal or distal stop to limit travel of an intravascular device (e.g. an embolic protection filter or probe) along the elongated member 18.

Flexible body 20 may include a first flat region 22, a bend region 24, and a second flat region 26. The first flat region 22 of flexible body 20 is distally sloped relative to the longitudinal axis of the elongated member 18, and includes a first opening 14. The second flat region 26 of flexible body 20, in turn, is proximally sloped relative to the longitudinal axis of the elongated member 18, and includes a second opening 16. The first and second flat regions 22,26 of flexible body 20 are configured to bend or flex about bend region 24 when subjected to an inwardly directed force F acting parallel to the longitudinal axis of the elongated member 18, orienting the first and second openings 14,16 in a direction that causes the leaf spring 12 to disengage from the elongated member 18.

The leaf spring 12 may be formed of any number of suitable biocompatible materials, including metals, metal alloys, polymers, or combinations thereof. For example, leaf spring 12 may comprise a metal or metal alloy such as stainless steel (e.g. type 304 or 316), platinum, titanium, tantalum, or other suitable materials. Examples of suitable polymeric materials include polyethylene terapthalate (PET), polytetraflouroethylene (PTFE), polyurethane (Nylon) fluorinated ethylene propylene (FEP), polyurethane, polypropylene (PP), polyvinylchloride (PVC), polyetherester, polyester, polyamide, elastomeric polyamides, block polyamide/ethers, polyether block amide (PEBA), silicones, polyethylene, polyether-ether ketone (PEEK), polyimide (PI), and polyetherimide (PEI). Polyether block amide (PEBA) is commercially available from Atochem Polymers of Birdsboro, Pa. under the trade name PEBAX.

In certain embodiments, leaf spring 12 may be formed of a superelastic or linear elastic material such as nickel-titanium alloy, allowing the leaf spring 12 to undergo substantial bending with relatively little strain. A leaf spring 12 comprising a superelastic material may permit greater flexion of the leaf spring 12, particularly in applications where the leaf spring 12 is repeatedly bent between the locked and unlocked positions.

As further shown in FIG. 1, leaf spring 12 may have an undulating shape formed by an indented region 28 of the flexible body 20. The reduction in width at the indented region 28 can be selected to impart a particular degree of flexibility to the leaf spring 12 at the bend region 24, depending on the particular application. For example, the width of the flexible body 18 at the indented region 28 can be relatively small in comparison to the width of the first and second flat regions 20,26, allowing greater flexion of the leaf spring 12 about the bend region 24.

Figure 2:
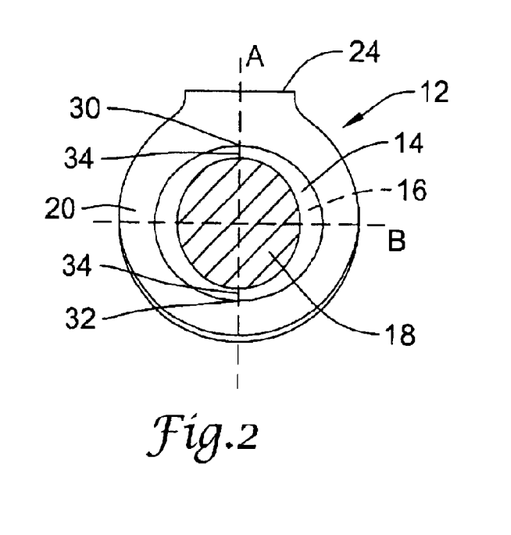
FIG. 2 is a view of the leaf spring along line 2—2 in FIG. 1.

FIG. 2 is a view of the leaf spring 12 along line 2—2 illustrated in FIG. 1, showing an end view of the leaf spring 12 in the unlocked position. As shown in FIG. 2, opening 14 may be elliptical in shape, having a major axis A and a minor axis B. Two contact regions 30,32 on the major axis A of opening 14 are configured to contact the elongated member 18 in the locked position, but are sufficiently spaced apart such that, when the leaf spring 12 is longitudinally compressed, a small clearance 34 is formed between each contact region 30,32 and the elongated member 18 allowing the elongated member 18 to pass therethrough. Opening 16, which is indicated by a phantom line in FIG. 2, may be dimensioned similarly as opening 14, providing a second set of contact regions on the second flat region 26 of flexible body 20.

The dimensions of the openings 14,16 can be selected to permit the passage of variously dimensioned elongated members 18. For example, the diameter of the openings 14,16 may be configured to receive an elongated member having an outer diameter, for example, of 0.008–0.037 inches, and more specifically 0.014–0.018 inches, corresponding to the size of many conventional guidewires used in the art. Moreover, while openings 14,16 are depicted as being elliptical in shape, those of skill in the art will recognize that other configurations are possible.

Figure 3:
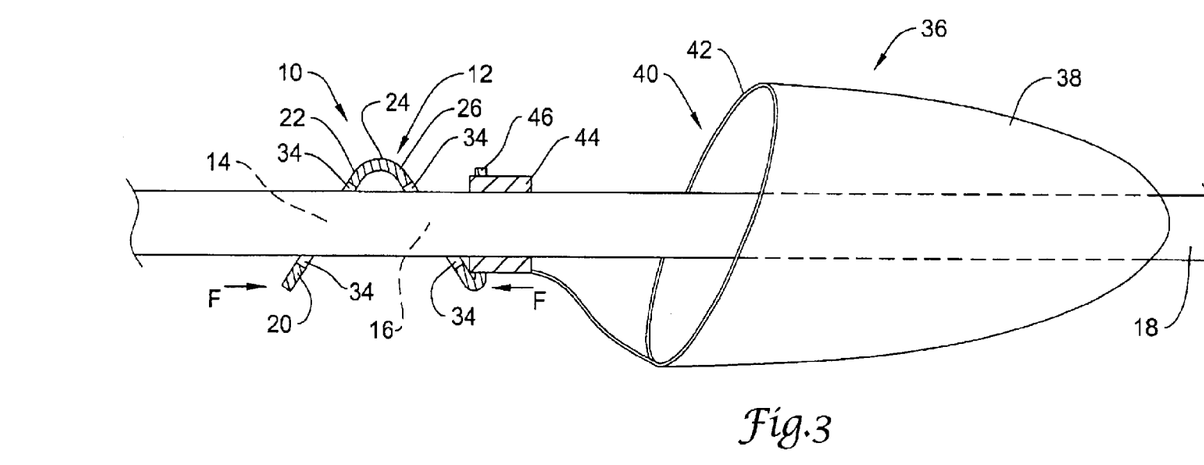
FIG. 3 is a partial cross-sectional view showing the leaf spring in a unlocked position along the elongated member.

FIG. 3 is a partial cross-sectional view showing the leaf spring 12 in an unlocked (i.e. compressed) position attached to an embolic protection filter 36. Embolic protection filter 36 may include an expandable filter membrane 38 coupled to a filter frame 40. The filter frame 40 may be formed of a wire loop 42 or other suitable support mechanism, and includes a support tube 44, which in the exemplary embodiment illustrated is attached to a third flat region 46 of the leaf spring 12. The support tube 44 is slidably and rotationally disposed about the elongated member 18 when leaf spring 12 is in an unlocked position, and releasably secured to the elongated member 18 when in the locked position.

As further illustrated in FIG. 3, when a compressive force F is applied longitudinally to compress the leaf spring 12 inwardly, the first and second flat regions 22,26 bend or flex about bend region 24, orienting the openings 14,16 at a greater angle relative to the longitudinal axis of the elongated member 18, forming a small clearance 34 between the periphery of the openings 14,16 and the outer surface of the elongated member 18. In this position, the embolic protection filter 36 and attached leaf spring 12 may be moved along the elongated member 18 and placed at a desired location within the patient's body. In an angioplasty procedure, for example, embolic protection filter 36 can be advanced along the elongated member 18 to a location distal a lesion located within a body lumen. The leaf spring 12 can then be locked onto the elongated member 18, and a therapeutic device advanced along the elongated member 18 to perform a therapeutic procedure such as percutaneous transluminal coronary angioplasty (PTCA) at a location proximal the embolic protection filter 36. At the conclusion of the procedure, or when the embolic protection filter 36 becomes occluded, the leaf spring 12 can be disengaged from the elongated member 18 and removed from the body.

Figure 4:
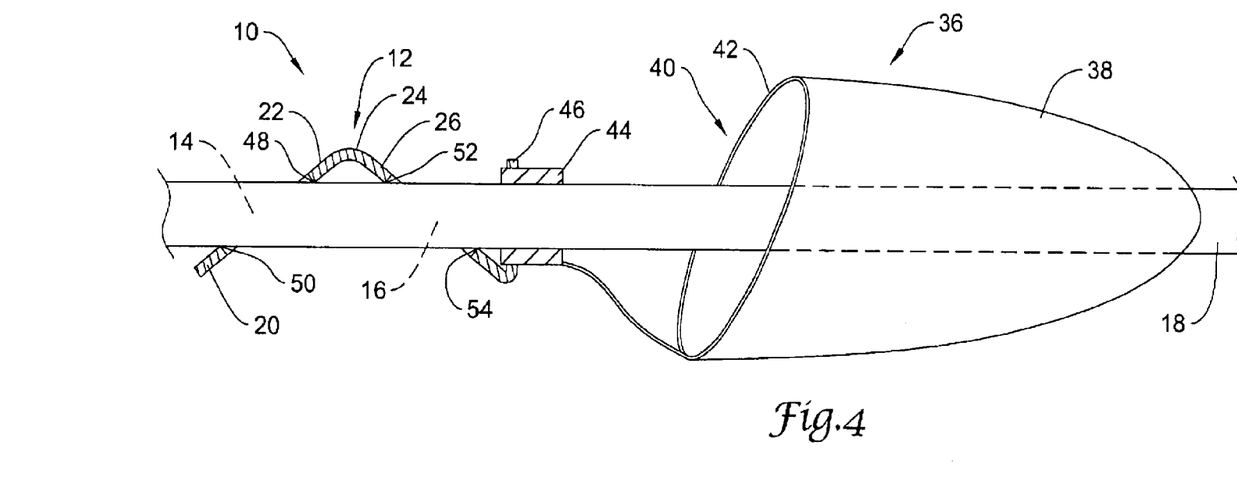
FIG. 4 is a partial cross-sectional view showing the leaf spring in a locked position along the elongated member.

FIG. 4 is a partial cross-sectional view showing the leaf spring 12 in a locked (i.e. uncompressed) position along the elongated member 18. In the absence of a compressive force acting on the leaf spring 12, the first and second flat regions 22,26 of flexible body 20 revert to their natural state and frictionally engage the elongated member 18. As shown in FIG. 4, the first flat region 22 slopes distally in a direction more parallel to the longitudinal axis of the elongated member 18, forming a first set of contact points 48,50 about the periphery of the first opening 14. Similarly, the second flat region 26 slopes proximally in a direction more parallel to the longitudinal axis of the elongated member 18, forming a second set of contact points 52,54 about the periphery of the second opening 16. In use, the first and second set of contact points 48,50,52,54 grip the elongated member 18, preventing movement of the elongated member 18 through the first and second openings 14,16.

Figure 5:
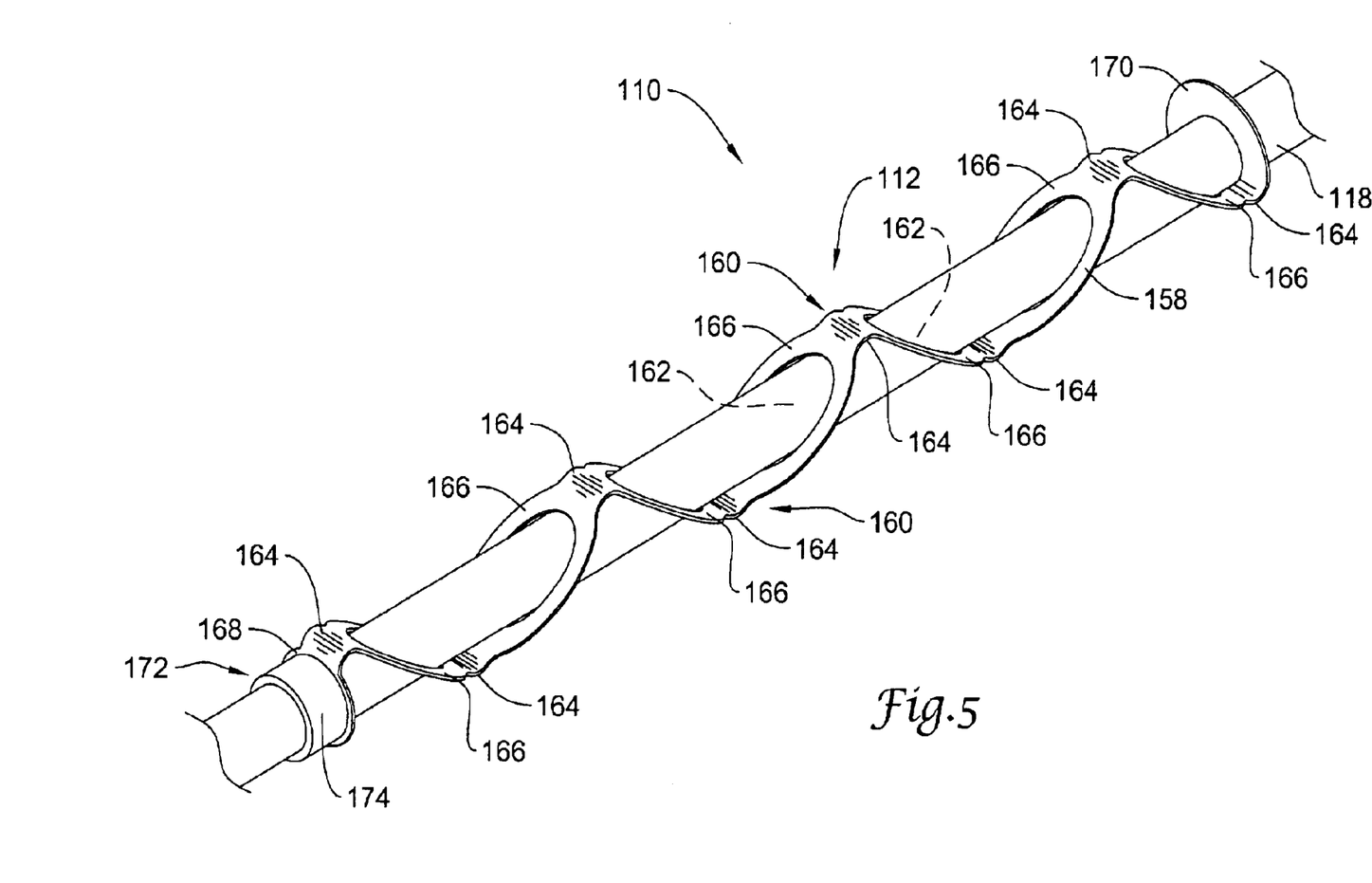
FIG. 5 is a perspective view of an anchoring mechanism in accordance with another exemplary embodiment of the present invention, wherein the anchoring mechanism comprises a multiple leaf spring.

Referring now to FIG. 5, an anchoring mechanism 110 in accordance with another exemplary embodiment of the present invention will now be described. Anchoring mechanism 110 comprises a multiple leaf spring 112 having a plurality of openings 162 configured to slidably and rotationally receive an elongated member 118 such as a guidewire or guide catheter. The multiple leaf spring 112 comprises a normally flat, flexible body 158 that can be deflected into a serpentine or saw-tooth shape when compressed in a direction substantially parallel to the longitudinal axis of the elongated member 118.

As with other embodiments described herein, multiple leaf spring 112 may have an undulating shape formed by one or more indented regions 160 of the flexible body 158. In addition, the materials used to form the multiple leaf spring 112 may selected to impart a particular degree of flexibility to the device. The multiple leaf spring 112 may be formed as a separate member and used as a proximal or distal stop, as shown in FIG. 5, or can be attached to or formed integrally with the intravascular device to directly secure the device to the elongated member 118.

The flexible body 158 may comprise a plurality of elongate regions 166 each having an opening 162 configured to slidably receive the elongated member 116 in an unlocked position, and frictionally engage the elongated member 118 in a locked position. Each opening 162 can be configured similar to the openings 14,16 depicted in FIG. 2, defining two contact regions along the major axis of the opening 162 that grip the elongated member 118 when multiple leaf spring 112 is in the locked position.

Flexible body 158 further comprises a number of bend regions 164 connecting the several elongate regions 166 together in alternating fashion such that each alternating elongate region 166 runs substantially parallel to each other. Each elongate region 166 is configured to bend in either a proximal or distal direction relative to the bend region 164, assuming a serpentine or saw-tooth shape when allowed to revert to its uncompressed (i.e. locked) position. In the exemplary embodiment illustrated in FIG. 5, flexible body 158 comprises eight alternating bend regions 164. However, it should be recognized that any number of bends 164 and/or elongate regions 166 may be utilized.

A proximal flat region 168 of multiple leaf spring 112 is configured to align perpendicularly to the elongated member 118 in both the locked and unlocked positions. The proximal flat region 168 includes an opening having an inner diameter slightly larger than the outer diameter of the elongated member 118, providing a clearance fit with the elongated member 118. In use, the clearance fit prevents the proximal flat region 168 from becoming misaligned or tilted about the elongated member 118 as the multiple leaf spring 112 is advanced along the elongated member 118 in the unlocked position. A distal flat region 170 of the flexible body 118 similarly includes an opening through the distal end of the multiple leaf spring 112 that provides a clearance fit when the device is in either the locked or unlocked positions, preventing misalignment of the distal portion of the leaf spring 112.

In any of the embodiments described herein, a centering bushing 172 may be used to further ensure that the leaf spring 12,112 is centered relative to the elongated member. In the embodiment of FIG. 5, for example, multiple leaf spring 112 may include a centering bushing 172 comprising a tubular shaft section 174 having an outer diameter configured to fit within the opening formed through proximal flat region 168, and an inner diameter configured to slidably receive the elongated member 118. A flanged section 176, illustrated in FIG. 6, can be used to fixedly secure the centering bushing 172 to the proximal flat region 168.

Figure 6:
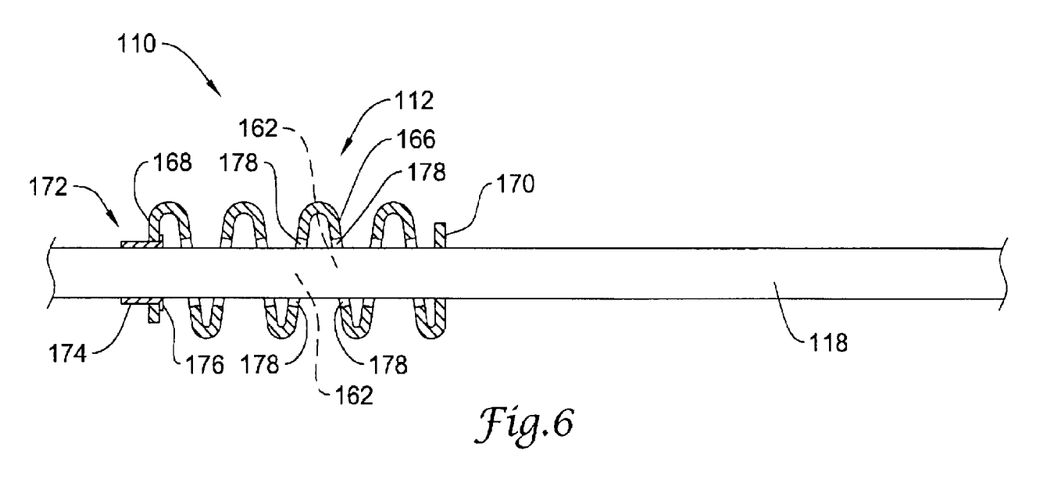
FIG. 6 is a partial cross-sectional view showing the multiple leaf spring in an unlocked position along the elongated member.

FIG. 6 is a partial cross-sectional view of multiple leaf spring 112, showing the multiple leaf spring 112 in an unlocked position along the elongated member 118. In an unlocked position shown in FIG. 6, the several elongate regions 166 are aligned at a greater angel relative to the longitudinal axis of the elongated member 118, forming a small clearance 178 between the periphery of each opening 162 and the outer surface of the elongated member 118.

Figure 7:
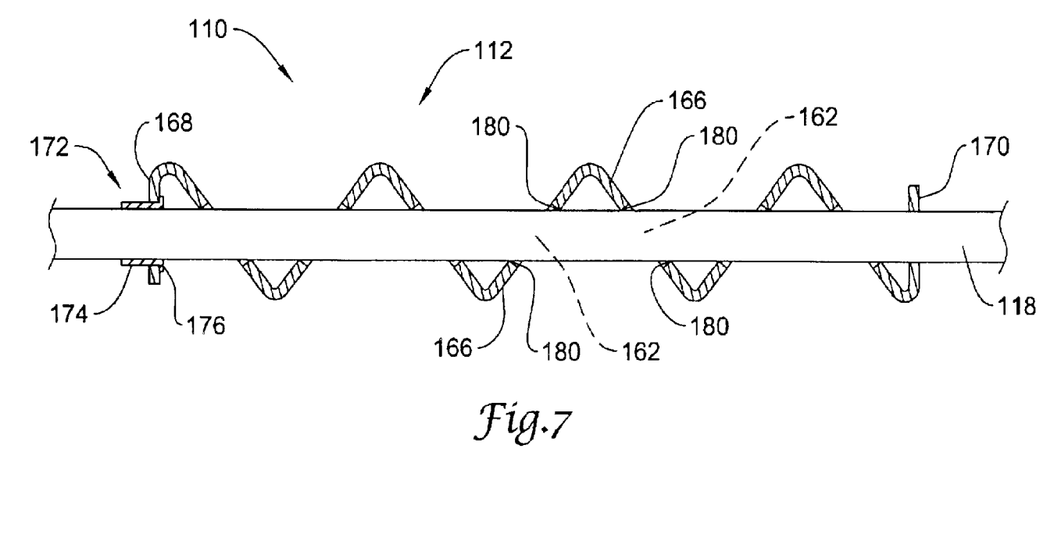
FIG. 7 is a partial cross-sectional view showing the multiple leaf spring in a locked position along the elongated member.

In a locked position illustrated in FIG. 7, the elongate regions 166 are allowed to expand longitudinally to their natural state and frictionally engage the elongated member 118. Each elongate region 166 slopes in alternating fashion in either a distal or proximal direction, orienting the respective openings 162 in a direction more parallel to the longitudinal axis of the elongated member 118. The change in alignment of the openings 162 caused by the expansion of the multiple leaf spring 112 creates several sets of contact regions 180 between the periphery of each opening 162 and the outer surface of the elongated member 118. In use, the contact regions 180 grip the elongated member 118, preventing movement of the elongated member 118 through the openings 162.

Figure 8:
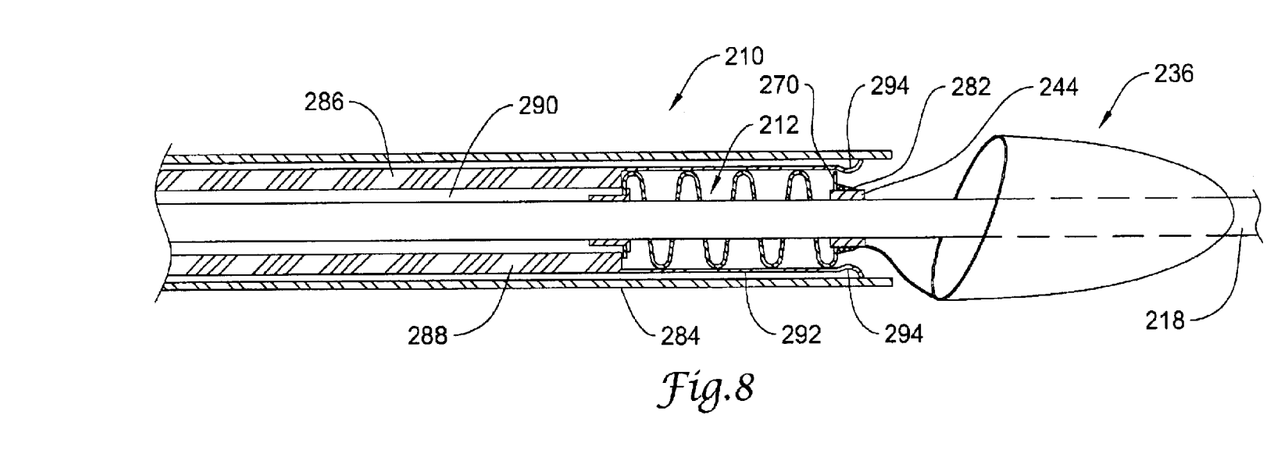
FIG. 8 is a partial cross-sectional view of an inner locking tube and delivery sheath in accordance with an exemplary embodiment of the present invention.

Referring now to FIG. 8, an anchoring mechanism 210 in accordance with another exemplary embodiment of the present invention will now be described in the context of a therapeutic procedure employing an embolic protection filter 236. Anchoring mechanism 210 comprises a multiple leaf spring 212 similar to that discussed above with respect to FIGS. 5–7, but further including a joint 282 at the distal flat region 270 connecting the multiple leaf spring 212 to a support tube 244 of the embolic protection filter 236. Joint 282 may be formed by soldering, welding, brazing, adhesive or other suitable bonding process and may be rotatable and/or slidable on an elongate member 218.

A delivery sheath 284 used to transport the embolic protection filter 236 in a collapsed position through the patient's vasculature is shown withdrawn proximally, with the filter membrane 236 in an expanded position. An inner locking tube 286 can be utilized to advance the multiple leaf spring 212 and embolic protection filter 236 along elongated member 218 (e.g. a guidewire) placed within the body. Inner locking tube 286 has a proximal section (not shown), a distal section 288, and an inner lumen 290 configured to slidably receive the elongated member 218. A distal segment 292 of the inner locking tube 286 has an enlarged inner diameter configured to constrain the multiple leaf spring 212 within a portion of the inner lumen 290. A locking tab(s) 294 on the inner locking tube 286 is configured to bend in an outward direction and engage the inner surface of the delivery sheath 284, maintaining the multiple leaf spring 212 in the unlocked position.

Figure 9:
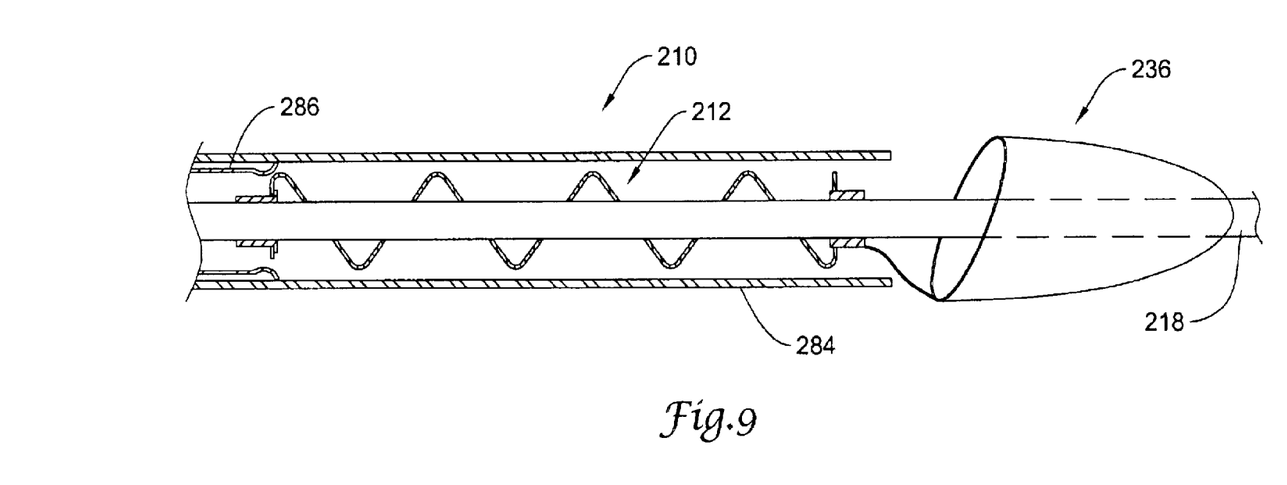
FIG. 9 is another partial cross-sectional view of the inner locking tube and delivery sheath of FIG. 8, showing the inner locking tube withdrawn proximally.

To engage the multiple leaf spring 212 and releasably secure the embolic protection filter 236 to the elongated member 218, inner locking tube 286 can be withdrawn proximally, causing the multiple leaf spring 212 to revert to its natural (i.e. uncompressed) state, as shown in FIG. 9. Once the multiple leaf spring 212 engages the elongated member 218, the inner locking tube 286 and delivery sheath 284 can be retracted proximally along the elongated member 218 and removed from the body.

Figure 10:
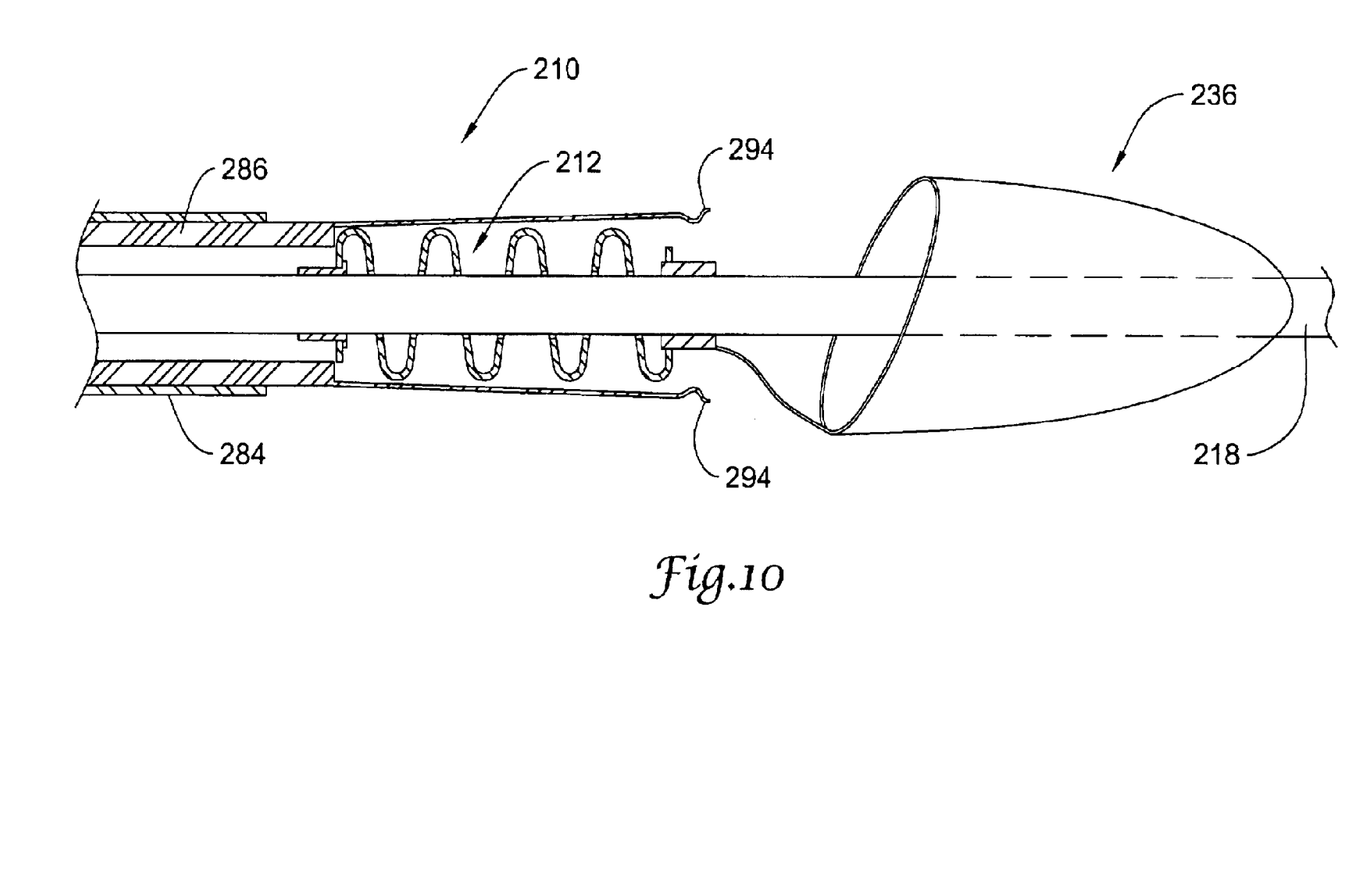
FIG. 10 is another partial cross-sectional view of the inner locking tube and delivery sheath of FIG. 8, showing the delivery sheath withdrawn proximally.

In an alternative method illustrated in FIG. 10, the inner locking tube 286 can be held stationary while the delivery sheath 284 is withdrawn proximally. As the delivery sheath 284 is withdrawn, the locking tab 294 at the distal end 288 of the distal segment 292 bends in an outward direction to permit withdrawal of the inner locking tube 286 in the proximal direction. The inner locking tube 286 and delivery sheath 284 can then be retracted proximally along the elongated member 218 and removed from the patient's body, if desired.

What is claimed is:

1. An intravascular filter device, comprising:
   a filter frame disposed about an elongated member;
   a filter membrane operatively coupled to the filter frame; and
   a leaf spring attached to the filter frame, said leaf spring comprising a flexible body having at least one opening configured to slidably and rotationally receive the elongated member in an unlocked position, and frictionally engage the elongated member in a locked position.

2. An intravascular filter device, comprising:
   a filter frame disposed about an elongated member;
   a filter membrane operatively coupled to the filter frame, said filter membrane being expandable between a collapsed position and an expanded position;
   a leaf spring attached to the filter frame, said leaf spring comprising a flexible body having at least one opening configured to slidably and rotationally receive the elongated member in an unlocked position, and frictionally engage the elongated member in a locked position;
   a locking tube configured to actuate the leaf spring between the unlocked and locked positions; and
   a delivery sheath configured to contain the filter membrane in the collapsed position.

* * * * *